(12) United States Patent
Feng (10) Patent No.: US 11,844,915 B2
(45) Date of Patent: Dec. 19, 2023

(54) BALLOON DILATATION SYSTEM

(71) Applicant: SURGSCIENCE (SHENZHEN) MEDICAL TECH. CO., LTD., Guangdong (CN)

(72) Inventor: Gengchao Feng, Guangdong (CN)

(73) Assignee: SURGSCIENCE (SHENZHEN) MEDICAL TECH. CO., LTD., Shenzhen (CN)

( * ) Notice: Subject to any disclaimer, the term of this patent is extended or adjusted under 35 U.S.C. 154(b) by 719 days.

(21) Appl. No.: 16/969,331

(22) PCT Filed: Apr. 28, 2018

(86) PCT No.: PCT/CN2018/084994
§ 371 (c)(1),
(2) Date: Aug. 12, 2020

(87) PCT Pub. No.: WO2019/153538
PCT Pub. Date: Aug. 15, 2019

(65) Prior Publication Data
US 2021/0046295 A1  Feb. 18, 2021

(30) Foreign Application Priority Data
Feb. 12, 2018 (CN) .......................... 201810145813.8

(51) Int. Cl.
*A61M 29/02* (2006.01)
*A61M 25/10* (2013.01)

(52) U.S. Cl.
CPC ...... *A61M 29/02* (2013.01); *A61M 25/10185* (2013.11); *A61M 2205/3331* (2013.01);
(Continued)

(58) Field of Classification Search
CPC ............ A61M 29/02; A61M 25/10185; A61M 25/1018; A61M 2205/3331;
(Continued)

(56) References Cited

U.S. PATENT DOCUMENTS

| | | | |
|---|---|---|---|
| 2005/0020870 A1* | 1/2005 | Suzuki | A61M 60/892 600/16 |
| 2009/0076439 A1* | 3/2009 | Dollar | A61M 25/1018 604/97.03 |
| 2010/0268154 A1* | 10/2010 | Vining | A61M 3/0258 604/26 |

FOREIGN PATENT DOCUMENTS

| | | |
|---|---|---|
| CN | 1933766 | 3/2007 |
| CN | 101015440 | 8/2007 |

(Continued)

OTHER PUBLICATIONS

International Search Report issued in PCT/CN2018/084994 dated Jun. 27, 2018.

*Primary Examiner* — Anh T Dang
(74) *Attorney, Agent, or Firm* — Workman Nydegger (57) ABSTRACT

Provided is a balloon dilatation system, which includes a signal collecting module, a main controller, a pressurization module, a pressure relief module, a first pressure sensor, a flow rate sensor, a balloon catheter and a balloon. The signal collecting module is electrically connected to the main controller, and is configured to collect a control signal and send the control signal to the main controller; the main controller is electrically connected to the pressurization module and the pressure relief module; the pressurization module is connected to the balloon through the balloon catheter; the pressure relief module is connected to the balloon through the balloon catheter; the first pressure sensor is arranged on the balloon catheter and is configured to monitor a first liquid pressure of the balloon; the flow rate
(Continued)

sensor is arranged on the balloon catheter and is configured to monitor a liquid flow rate of the balloon catheter.

20 Claims, 3 Drawing Sheets

(52) U.S. Cl.
CPC ............... *A61M 2205/3334* (2013.01); *A61M 2205/505* (2013.01); *A61M 2210/12* (2013.01)

(58) Field of Classification Search
CPC .... A61M 2205/3334; A61M 2205/505; A61M 2210/12
See application file for complete search history.

(56) References Cited

FOREIGN PATENT DOCUMENTS

| CN | 202960636 | 6/2013 |
| CN | 104349804 | 2/2015 |
| CN | 106535954 | 3/2017 |

\* cited by examiner

BALLOON DILATATION SYSTEM

CROSS-REFERENCE TO RELATED APPLICATIONS

This Application is a 371 application of International Patent Application No. PCT/CN2018/084994, filed Apr. 28, 2018, which claims the benefit of Chinese Patent Application No. 201810145813.8, filed on Feb. 12, 2018, which applications are incorporated herein by reference in their entirety.

TECHNICAL FIELD

Embodiments of the present application relate to a medical device technology, for example, to a balloon dilatation system.

BACKGROUND

As the prevalence rate of cardiovascular diseases increases year by year, methods for treating the cardiovascular diseases by using balloon dilatation are used in clinical applications in varieties of ways. For example, in cardiovascular stenosis and occlusion operations, contrast agent or normal saline can be injected into the balloon in a manner of pressurization, so that digital subtraction angiography (DSA) equipment can clearly monitor the surgical treatment and determination of the affected part of a patient and at the same time, can also pressurize or relieve the pressure of the balloon used by the dilation stent for dilating the affected part of a blood vessel, and the balloon is dilated or contracted, achieving the purpose of dilating the blood vessel or releasing the stent.

The balloon on the market adopts a low-precision mechanical pressure gauge, and the risk of blood vessel rupture caused by pressurization exists in clinic.

SUMMARY

The present application provides a balloon dilation system to improve safety during a balloon dilation process.

A balloon dilation system is provided in an embodiment of the present application and includes a signal collecting module, a main controller, a pressurization module, a pressure relief module, a first pressure sensor, a flow rate sensor, a balloon catheter and a balloon.

The signal collecting module is electrically connected to the main controller, and is configured to collect a control signal and send the control signal to the main controller.

The main controller is electrically connected to the pressurization module and the pressure relief module separately, and is configured to receive the control signal and control a working state of the pressurization module and a working state of the pressure relief module according to the control signal.

The pressurization module is connected to the balloon through the balloon catheter, and is configured to inject liquid into the balloon through the balloon catheter according to a first control signal of the main controller.

The pressure relief module is connected to the balloon through the balloon catheter, and is configured to discharge liquid in the balloon catheter and the balloon according to a second control signal of the main controller.

The first pressure sensor is arranged on the balloon catheter, and electrically connected to the main controller; and is configured to monitor a first liquid pressure of the balloon and send the first liquid pressure to the main controller.

The flow rate sensor is arranged on the balloon catheter, and electrically connected to the main controller; and is configured to monitor a liquid flow rate of the balloon catheter and send the liquid flow rate to the main controller.

The main controller is further configured to perform at least one of the operations described below.

At least one of the following steps is performed according to the first liquid pressure: adjusting the working state of the pressurization module or adjusting the working state of the pressure relief module.

At least one of the following steps is performed according to the liquid flow rate: adjusting the working state of the pressurization module or adjusting the working state of the pressure relief module.

In an embodiment, the main controller is configured to perform at least one of the steps described below.

In response to the first liquid pressure being greater than a first pressure value, the pressurization module is closed and the pressure relief module is opened.

In response to determining, according to the liquid flow rate, that a capacity of liquid in the balloon is greater than a first capacity, the pressurization module is closed and the pressure relief module is opened.

In an embodiment, the balloon catheter is provided with a safety valve, and in response to the first liquid pressure being greater than or equal to a second pressure value or in response to determining, according to the liquid flow rate, that the capacity of liquid in the balloon is greater than a second capacity, the safety valve is closed and liquid injection into the balloon is stopped.

In an embodiment, the first pressure sensor is further configured to monitor a pressure value of a balloon wall during a pressurization process or a pressure relief process and send the pressure value of the balloon wall to the main controller.

The main controller is further configured to identify moments when the pressure value of the balloon wall is equal to zero, sort a liquid pressure corresponding to each of the moments from large to small, determine a liquid pressure at a first position of the sorting as a systolic pressure of a blood vessel, and determine a liquid pressure at an end position of the sorting as a diastolic pressure of the blood vessel.

The balloon is arranged inside a blood vessel.

In an embodiment, the main controller is further configured to determine a current balloon radius according to the capacity of liquid in the balloon and a balloon parameter during the pressurization process or the pressure relief process and to determine a sum of a balloon radius and a balloon thickness as a radius of the blood vessel.

In an embodiment, the main controller is further configured to determine an expansion coefficient of a blood vessel according to the capacity of liquid in the balloon and the first liquid pressure during a pressurization process or a pressure relief process and to determine blood vessel elasticity according to the expansion coefficient of the blood vessel.

In an embodiment, the main controller is further configured to determine a pressurization resistance according to the first liquid pressure and a liquid flow velocity during a pressurization process, where the liquid flow velocity is determined by the liquid flow rate.

In an embodiment, the system further includes a second pressure sensor connected to a liquid storage device and the main controller and configured to detect a second liquid pressure of the liquid storage device.

In an embodiment, the system further includes a display electrically connected to the main controller and configured to display dilation parameters during the pressurization process and the pressure relief process, where the dilation parameters include the first liquid pressure and the liquid flow rate.

In an embodiment, the signal collecting module includes a pedal controller electrically connected to the main controller and configured to collect a pedal control signal and send the pedal control signal to the main controller.

In an embodiment, the signal collecting module includes an information input sub-module connected to the main controller and configured to determine the control signal according to an external input command and send the control signal to the main controller.

According to the balloon dilatation system provided by the embodiments of the present application, the first pressure sensor and the flow rate sensor are arranged to monitor in real time the first liquid pressure and the capacity of liquid injected into the balloon. When the main controller detects that the first liquid pressure and the liquid capacity are abnormal, the working state of at least one of the pressurization module or the pressure relief module is adjusted to adjust the first liquid pressure or the liquid capacity to a normal range, thus improving the safety in the dilation process of the affected part.

DETAILED DESCRIPTION

The present application will be further described with reference to the drawings and embodiments. It is to be understood that the embodiments set forth below are intended to illustrate and not to limit the present application. It is to be noted that to facilitate description, only part, not all, of structures related to the present application are illustrated in the drawings.

Embodiment One

Figure 1:
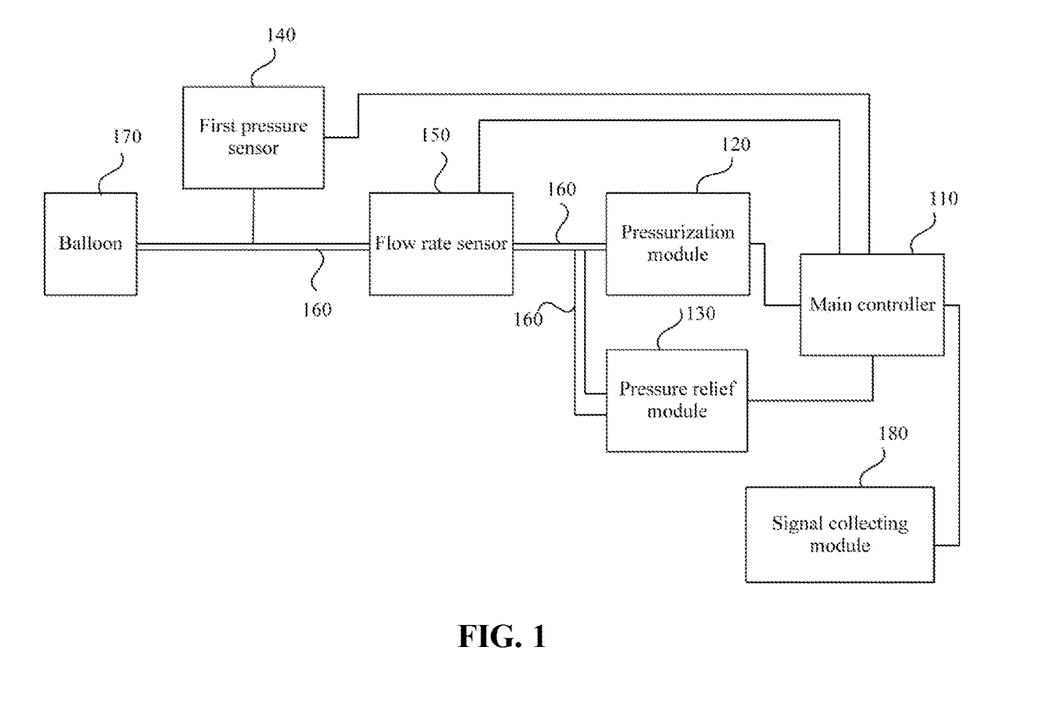
FIG. 1 is a structural diagram of a balloon dilatation system according to embodiment one.

FIG. 1 is a structural diagram of a balloon dilatation system according to embodiment one. This embodiment can be applied to the case where the balloon is dilated through injection of liquid into the balloon by pressurization, and can be applied to balloon dilation operations for treating cardiovascular diseases. Referring to FIG. 1, the balloon dilation system includes a signal collecting module 180, a main controller 110, a pressurization module 120, a pressure relief module 130, a first pressure sensor 140, a flow rate sensor 150, a balloon catheter 160 and a balloon 170.

The signal collecting module 180 is electrically connected to the main controller 110, and is configured to collect a control signal and send the control signal to the main controller 110.

The main controller 110 is electrically connected to the pressurization module 120 and the pressure relief module 130 separately, and is configured to receive the control signal and control a working state of the pressurization module 120 and a working state of the pressure relief module 130 according to the control signal.

The pressurization module 120 is connected to the balloon 170 through the balloon catheter 160, and is configured to inject liquid into the balloon 170 through the balloon catheter 160 according to a first control signal of the main controller 110.

The pressure relief module 130 is connected to the balloon through the balloon catheter 160, and is configured to discharge liquid in the balloon catheter 160 and the balloon 170 according to a second control signal of the main controller 110.

The first pressure sensor 140 is arranged on the balloon catheter 160 and electrically connected to the main controller 110, and is configured to monitor a first liquid pressure of the balloon 170 and send the first liquid pressure to the main controller 110.

The flow rate sensor 150 is arranged on the balloon catheter 160 and electrically connected to the main controller 110, and is configured to monitor a liquid flow rate of the balloon catheter 160 and send the liquid flow rate to the main controller 110.

The main controller 110 is further configured to perform at least one of the operations described below.

At least one of the following steps is performed according to the first liquid pressure: adjusting the working state of the pressurization module 120 or adjusting the working state of the pressure relief module 130.

At least one of the following steps is performed according to the liquid flow rate: adjusting the working state of at least one of the pressurization module 120 or the pressure relief module 130.

In this embodiment, the signal collecting module 180 may acquire a control signal. The control signal may be determined through an external input command or through sensing of a pressure applied by a user to the signal collecting module. The signal collecting module 180 sends the acquired control signal to the main controller 110. The main controller 110 controls the working states of the pressurization module 120 and the pressure relief module 130 according to the control signal. The working state of the pressurization module 120 includes the activated states of different pressurization parameters and the closed state, and the working state of the pressure relief module 130 includes the activated states of different pressure relief parameters and the closed state. When the pressurization module 120 is in the activated state, liquid is injected into the balloon 170 through the balloon catheter 160; when the pressure relief module 130 is in the activated state, liquid in the balloon catheter 160 and the balloon 170 is discharged. The liquid may be contrast agent or normal saline.

In this embodiment, as liquid is injected, pressure is generated in the balloon catheter. When the balloon dilatation system is applied to the affected part which may be, for example, a blood vessel, the blood vessel is easily ruptured when the liquid pressure in the balloon is too high. The first pressure sensor 140 is electrically connected to the balloon catheter 160, acquires the first liquid pressure of the balloon in real time, and sends the first liquid pressure to the main controller 110. The balloon catheter 160 is in communication with the balloon 170, that is, the balloon catheter 160 and the balloon 170 have the same liquid pressure. The first pressure sensor 140 is connected to the balloon catheter 160 so that the first liquid pressure of the balloon 170 can be acquired.

The flow rate sensor 150 is arranged in series on the balloon catheter 160 and can monitor the flow rate of liquid in the balloon catheter 160. The liquid flow rate is the volume of liquid passing through the balloon catheter 160 within a preset time. The preset time may be, for example, 1s.

The capacity of liquid injected into the balloon 170 can be determined based on the liquid flow rate of the balloon catheter 160 and time and is sent to the main controller 110. The main controller 110 monitors the first liquid pressure and the liquid capacity, and when one of the first liquid pressure or the liquid capacity exceeds a safety range, the working state of at least one of the pressurization module 120 or the pressure relief module 130 is adjusted to adjust the first liquid pressure or the liquid capacity to the safety range.

In this embodiment, the first pressure sensor and the flow rate sensor are arranged to monitor in real time the pressure and the capacity of liquid injected into the balloon. When the main controller detects that the liquid pressure or the liquid capacity exceeds the safety range, the working state of at least one of the pressurization module or the pressure relief module is adjusted to adjust the first liquid pressure or the liquid capacity to the safety range, thus improving the safety in the dilation process of the affected part.

Optionally, the main controller 110 is configured to: if the first liquid pressure is greater than the first pressure value, close the pressurization module 120 and open the pressure relief module 130.

The first pressure value is a safety pressure value of the current position of the balloon, and may be determined according to the current position of the balloon. When the main controller 110 identifies that the first liquid pressure is greater than the first pressure value, the pressurization module 120 is closed, the injection of liquid into the balloon 170 is stopped, and the pressure relief module 130 is opened to discharge the liquid in the balloon catheter 160 and the balloon 170, thus reducing the first liquid pressure and avoiding rupture of the affected part caused by excessive first liquid pressure.

Optionally, if the capacity of liquid in the balloon 170 is determined to be greater than the first capacity according to the liquid flow rate, the pressurization module 120 is closed and the pressure relief module 130 is opened.

The first capacity is the capacity threshold of the balloon 170. When the liquid capacity is greater than the first capacity, the pressurization module 120 is closed, the injection of liquid into the balloon 170 is stopped, and the pressure relief module 130 is opened to discharge the liquid in the balloon catheter 160 and the balloon 170, thus reducing the capacity of liquid in the balloon 170 and avoiding rupture of the affected part caused by excessive liquid capacity.

Figure 2:
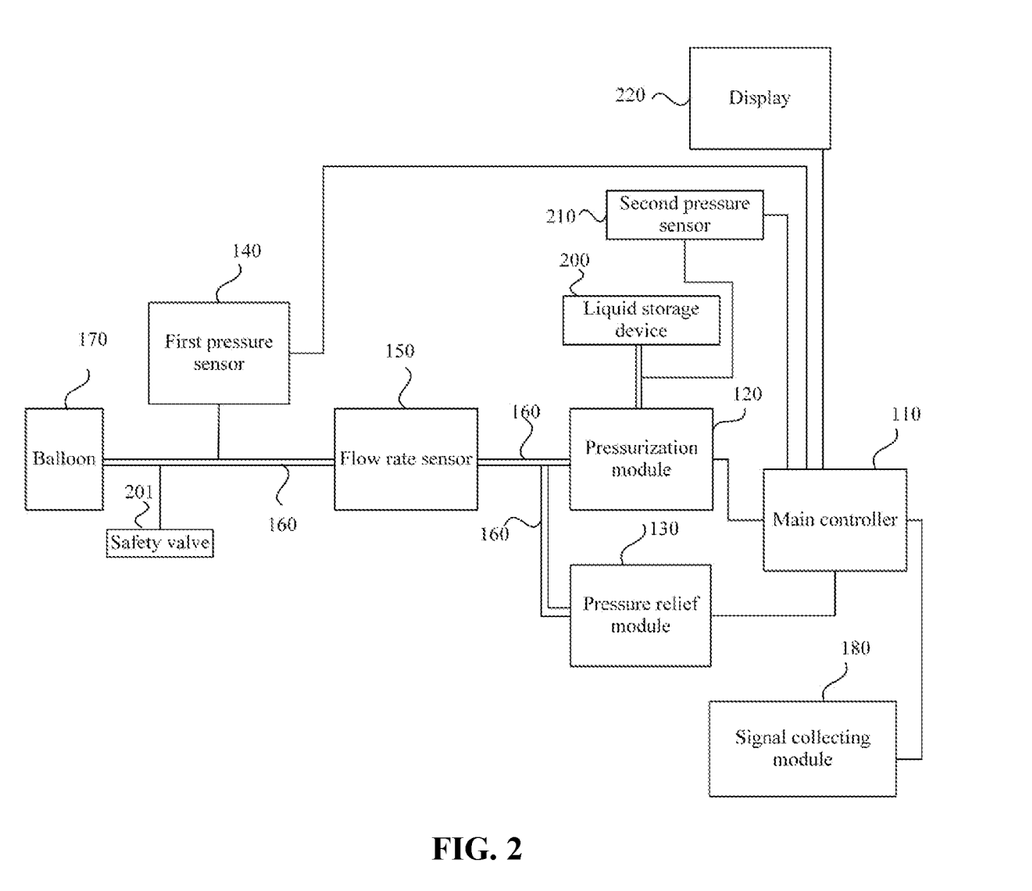
FIG. 2 is a structural diagram of another balloon dilatation system according to embodiment one.

Optionally, the balloon catheter 160 is provided with a safety valve 201, and when the first liquid pressure is greater than or equal to a second pressure value or when it is determined that the capacity of liquid in the balloon 170 is greater than a second capacity according to the liquid flow rate, the safety valve 201 is closed and liquid injection into the balloon 170 is stopped.

The second pressure value is a safety pressure value of the current position of the balloon 170 and may be the same as the first pressure value. The second capacity is the safety capacity of the current position of the balloon 170. Optionally, the second capacity may be determined according to the safety dilation diameter of the current position of the balloon 170. The safety dilation diameter is the maximum diameter that the current position of the balloon 170 reaches within the safety range, the maximum diameter of the balloon 170 is determined according to the difference between the safety dilation diameter and the thickness of the balloon wall, the balloon 170 may be regarded as a regular cylindrical structure, and the second capacity can be determined according to the calculation formula of the balloon height and volume.

When the first liquid pressure is greater than or equal to the second pressure value, or when the capacity of liquid in the balloon 170 is determined to be greater than the second capacity according to the liquid flow rate, i.e., when the safety range is exceeded, the safety valve 201 is closed, the injection of liquid into the balloon 170 is stopped, and the safety during the dilation process of the balloon 170 is improved. Optionally, when the safety valve 201 is closed, the pressure relief module 130 is activated to discharge the liquid in the balloon catheter 160 and the balloon 170, reducing the pressure of liquid in the balloon catheter 160 so that the pressure is within a safety range.

Optionally, the first pressure sensor 140 is further configured to monitor a pressure value of a balloon wall during a pressurization process or a pressure relief process and send the pressure value of the balloon wall to the main controller 110.

The main controller 110 is further configured to identify moments when the pressure value of the balloon wall is equal to zero, sort a liquid pressure corresponding to each of the moments from large to small, determine a liquid pressure at a first position of the sorting as a systolic pressure of a blood vessel, and determine a liquid pressure at an end position of the sorting as a diastolic pressure of the blood vessel. The balloon 170 is arranged inside a blood vessel.

In this embodiment, the pressurization process refers to a process in which the pressurization module 120 injects liquid into the balloon 170 under the control of the main controller 110 to increase the pressure of the liquid in the balloon 170; the pressure relief process refers to a process in which the pressure relief module 130 discharges the liquid in the balloon 170 under the control of the main controller 110 to reduce the pressure of the liquid in the balloon 170.

According to the principle of interaction force, when the two sides of the balloon wall receive two forces with opposite directions and the same magnitude, the total force on the balloon wall is zero. Therefore, when the total force on the balloon wall is zero, the inside liquid pressure is the same as the blood pressure. The blood pressure includes a blood pressure of a blood vessel and a systolic pressure of the blood vessel due to heart beating, the diastolic pressure of the blood vessel is the minimum value of human blood pressure and the systolic pressure of the blood vessel is the maximum value of human blood pressure. During a pressurization process or a pressure relief process, moments when the pressure value of the balloon wall is equal to zero and a liquid pressure corresponding to each of the moments are monitored. The plurality of liquid pressures is sorted from large to small or from small to large. The minimum liquid pressure is determined as the diastolic pressure of the blood vessel, and the maximum liquid pressure is determined as the systolic pressure of the blood vessel.

In this embodiment, when the dilation operation is performed on the blood vessel, the blood pressure of the affected part can be simultaneously acquired during the pressurization process or the pressure relief process, and no other blood pressure measurement equipment is needed, so that the operation is performed conveniently and fast, and the efficiency of the blood vessel operation is improved.

Optionally, the main controller 110 is further configured to determine a current balloon diameter according to the liquid capacity and a balloon parameter and determine a sum of a balloon diameter and a balloon thickness as the diameter of a dilation target.

The balloon parameter is a morphological parameter of the balloon 170, and optionally, the balloon 170 has a cylindrical structure, and the balloon parameter includes the height and thickness of the balloon 170. The main controller 110 can determine the radius r of the balloon 170 according to the liquid capacity of the balloon 170 and height of the balloon 170 at the critical time, so that it is known that the radius of the dilation target is R=r+h, where h is the thickness of the balloon. The dilation target may be, for example, a blood vessel.

The above method of determining the radius of the blood vessel is suitable for the case where the balloon 170 is in contact with the dilation target.

Optionally, the liquid is normal saline. The diameters of the dilation target at different moments can be determined according to the capacity of liquid injected into the balloon 170 without determination of the diameter of the dilation target by radiography of the injected contrast agent. The harm of radiography to human body is reduced. The cost and time consumption caused by frequent radiography is reduced. The safety and efficiency are improved.

Optionally, the main controller 110 is further configured to determine an expansion coefficient of a blood vessel according to the capacity of liquid in the balloon and the first liquid pressure during a pressurization process or a pressure relief process and determine the blood vessel elasticity according to the expansion coefficient of the blood vessel.

The expansion coefficient K=V/P, where the unit of the expansion coefficient K is ml/cmH$_2$O, V is the liquid capacity, and P is the first liquid pressure. The blood vessel elasticity can be determined according to the expansion coefficient. The larger the expansion coefficient corresponding to the same liquid capacity, the better the blood vessel elasticity. Accordingly, the smaller the expansion coefficient, the worse the blood vessel elasticity. In this embodiment, the system evaluates the blood vessel elasticity while the blood vessel is being dilated.

Optionally, the main controller 110 is further configured to determine a pressurization resistance according to the first liquid pressure and a liquid flow velocity during a pressurization process, where the liquid flow velocity is determined by the liquid flow rate.

The pressurization resistance F=P/Q, P is the first liquid pressure and Q is the liquid flow velocity. The main controller 110 monitors the pressurization resistance in the balloon 170 and the balloon catheter 160. When the pressurization resistance is greater than the safety resistance, a problem exists that blood vessel rupture is caused by excessive resistance. The main controller 110 adjusts the liquid flow velocity according to the pressurization resistance so that the pressurization resistance is within the safety range, thus improving the safety during the pressurization process.

Referring to FIG. 2, FIG. 2 is a structural diagram of a balloon dilatation system according to embodiment one. In an embodiment, the system further includes a second pressure sensor 210 connected to a liquid storage device 200 and the main controller 110 and configured to detect a second liquid pressure of the liquid storage device 200. The liquid storage device 200 refers to a device for storing stock solution, is connected to the pressurization module 120, and is configured to supply liquid to the pressurization module 120. The second pressure sensor 210 identifies the remaining amount of liquid in the liquid storage device 200 by detecting the second liquid pressure of the liquid storage device 200. Optionally, the liquid storage device 200 may be deformed such that when the liquid in the liquid storage device 200 is full, the second liquid pressure is zero, and when the liquid is withdrawn, the second liquid pressure decreases.

In this embodiment, the second pressure sensor 210 sends the second liquid pressure to the main controller 110, so that the main controller 110 monitors the remaining amount of liquid in the liquid storage device 200 according to the second liquid pressure, and timely provides a reminder according to the remaining amount of liquid, so as to avoid problems such as operation interruption caused when the liquid remaining amount of the liquid storage device 200 is zero.

Optionally, the system further includes a display 220 electrically connected to the main controller 110 and configured to display dilation parameters during the pressurization process and the pressure relief process, where the dilation parameters include the first liquid pressure and the liquid flow rate.

In this embodiment, the display 220 is configured to display the dilation parameters acquired by the main controller 110, and to form a display curve according to different dilation parameters. The dilation parameters include, but are not limited to, the liquid flow rate, the liquid pressure, the blood vessel pressure, and the diameter and the capacity of the dilation target. The display curve includes, but is not limited to, a liquid flow rate-pressure curve, a liquid flow rate-time curve, a liquid pressure-time curve, a liquid capacity-pressure curve, and a liquid capacity-time curve. Through the display 220, medical personnel can intuitively and clearly acquire parameter changes in the balloon dilation process, facilitating improvement of the success rate of the operation.

Figure 3:
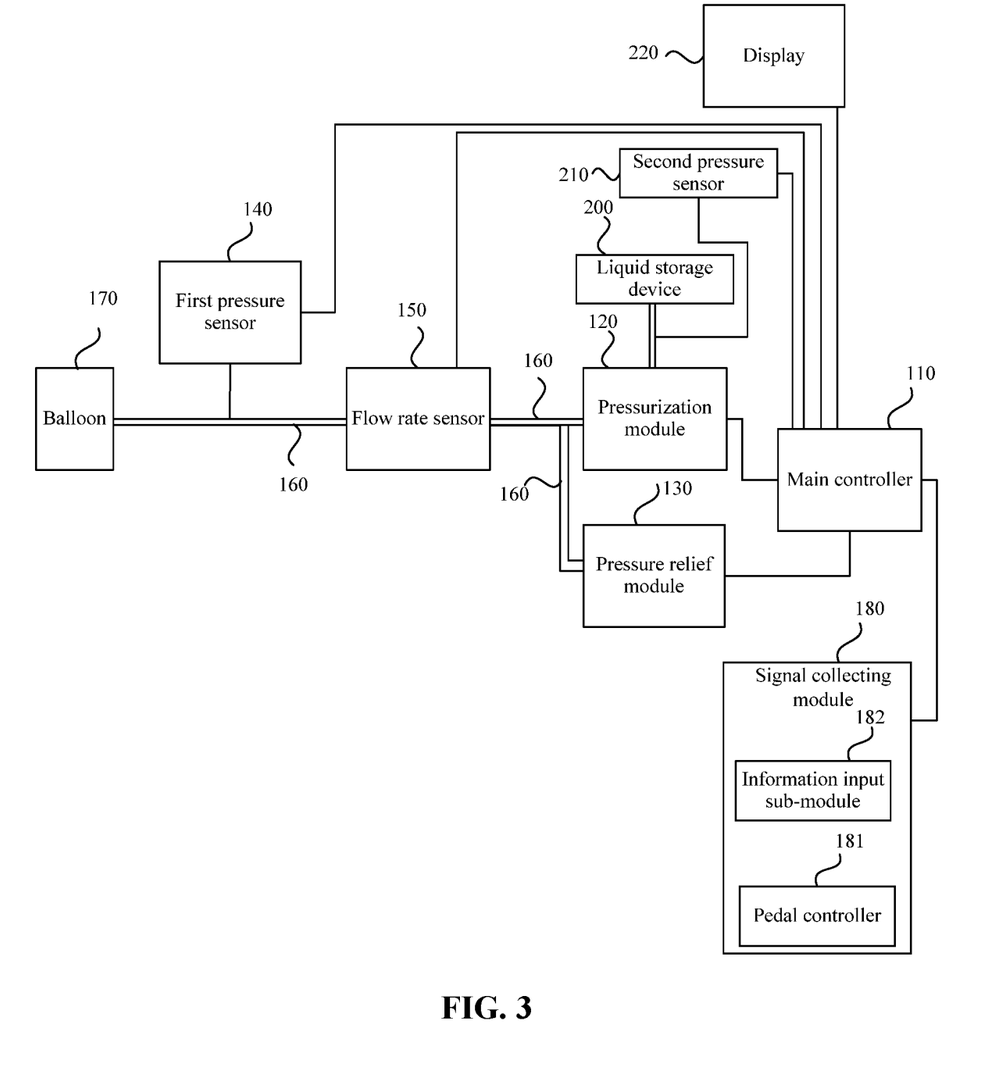
FIG. 3 is a structural diagram of another balloon dilatation system according to embodiment one.

Optionally, referring to FIG. 3, the signal collecting module 180 includes a pedal controller 181, where the pedal controller 181 is electrically connected to the main controller 110 and is configured to collect a pedal control signal and send the control signal to the main controller 110.

In this embodiment, the control signal collecting module 180 can automatically collect control signals without the need for medical personnel to continuously manually operate the balloon 170. The control signal collected by the pedal controller 181 may be adjusted according to the stepping pressure degree of the foot, and may also be adjusted according to the operation purpose of pressurizing or releasing the balloon 170. Optionally, the pedal controller 181 includes a pressure sensor, a first key unit, and a first processor. The pressure sensor is electrically connected to the first processor and configured to collect a pressure signal of the foot in real time and send the pressure signal to the first processor in real time. The first key unit is electrically connected to the first processor and configured to send key information of the pressed key to the first processor. The first processor is electrically connected to the pressure sensor, the first key unit and the main controller 110 and configured to generate a corresponding control signal according to the received pressure signal and key information and send the control signal to the main controller 110. The first key unit includes a first pressurization key and a first pressure relief key which are respectively used for generating pressurization key information and pressure relief key information.

In this embodiment, the pressure signal of the foot can be changed in real time through adjustment of the stepping pressure degree of the foot according to actual requirements, and optionally, the pressure signal is proportional to the stepping pressure degree of the foot. According to the operation of pressurizing or releasing the balloon, the pressed key in the first key unit is selected, and then corresponding key information is generated according to the pressed key and sent to the first processor to determine the control signal. Through the setting of the pedal controller, the control signal automatically collected through the foot action is sent to the pressurization module or the pressure relief module, and the balloon does not need to be pressurized or relieved by hands, thus freeing the hands, simplifying the operation and saving manpower and physical strength.

Optionally, the signal collecting module 180 includes an information input sub-module 182, where the information input sub-module is connected to the main controller 110 and is configured to determine the control signal according to an external input command and send the control signal to the main controller 110.

The information input sub-module 182 includes a touch display and a second processor. The touch display is configured to collect and display an external input touch command. The second processor is electrically connected to the touch display and the controller 110, and is configured to generate a control signal according to the external input touch command and send the control signal to the main controller 110. The external input touch command may be a pressure change rate and operation identifier input by a user on the touch display according to actual requirements. The operation identifiers may be a pressurization identifier and a pressure relief identifier.

The information input sub-module 182 may further include a pressure adjustment key, a second pressurization key, and a second pressure relief key, i.e., an external input command may also be input through a key. Accordingly, the second processor is configured to generate control signals according to key information corresponding to the pressure adjustment key, the second pressurization key and the second pressure relief key respectively, and send the control signals to the main controller 110.

A control signal is determined according to an external input command, and the main controller controls the working states of the pressurization module and the pressure relief module according to the control signal, so as to inject liquid into the balloon or discharge liquid in the balloon through the balloon catheter. Through the setting of the information input sub-module, only one hand is needed to operate, which is more convenient and fast and also saves manpower and physical strength.

In an embodiment, the signal collecting module 180 may simultaneously include the information input sub-module 182 and the pedal controller 181, and the information input sub-module 182 and the pedal controller 181 may be switched for application according to clinical requirements.

Exemplarily, referring to FIG. 3, FIG. 3 is a structural diagram of a balloon dilatation system according to embodiment one, and the information input sub-module 182 and the pedal controller 181 are simultaneously included. FIG. 3 is merely one implementation. In other embodiments, the system may include merely one of the information input sub-module 182 or the pedal controller 181.

INDUSTRIAL APPLICABILITY

According to the balloon dilatation system provided by the embodiments of the present application, when the main controller detects that the first liquid pressure and the liquid capacity are abnormal, the working state of at least one of the pressurization module or the pressure relief module is adjusted to adjust the first liquid pressure or the liquid capacity to a normal range, thus improving the safety in the dilation process of the affected part.

What is claimed is:

1. A balloon dilation system, comprising a signal collecting module, a main controller, a pressurization module, a pressure relief module, a first pressure sensor, a flow rate sensor, a balloon catheter, and a balloon; wherein:
   the signal collecting module is electrically connected to the main controller, and is configured to collect a control signal and send the control signal to the main controller;
   the main controller is electrically connected to the pressurization module and the pressure relief module separately, and is configured to receive the control signal and control a working state of the pressurization module and a working state of the pressure relief module according to the control signal;
   the pressurization module is connected to the balloon through the balloon catheter, and is configured to inject liquid into the balloon through the balloon catheter according to a first control signal of the main controller;
   the pressure relief module is connected to the balloon through the balloon catheter, and is configured to discharge liquid in the balloon catheter and the balloon according to a second control signal of the main controller;
   the first pressure sensor is arranged on the balloon catheter, and electrically connected to the main controller; and is configured to monitor a first liquid pressure of the balloon and send the first liquid pressure to the main controller;
   the flow rate sensor is arranged on the balloon catheter, and electrically connected to the main controller; and is configured to monitor a liquid flow rate of the balloon catheter and send the liquid flow rate to the main controller;
   the main controller is configured to determine a pressurization resistance according to the first liquid pressure and a liquid flow velocity during a pressurization process, wherein the liquid flow velocity is determined by the liquid flow rate; and
   the main controller is further configured to perform at least one of following operations:
   performing at least one of following steps according to the first liquid pressure: adjusting the working state of the pressurization module or adjusting the working state of the pressure relief module; or
   performing at least one of the following steps according to the liquid flow rate: adjusting the working state of the pressurization module or adjusting the working state of the pressure relief module.

2. The system of claim 1, wherein the main controller is configured to perform at least one of following steps:
   in response to the first liquid pressure being greater than a first pressure value, closing the pressurization module and opening the pressure relief module; or
   in response to determining, according to the liquid flow rate, that a capacity of liquid in the balloon is greater than a first capacity, closing the pressurization module and opening the pressure relief module.

3. The system of claim 2, wherein the balloon catheter is provided with a safety valve, and in response to the first liquid pressure being greater than or equal to a second pressure value or in response to determining, according to the liquid flow rate, that the capacity of liquid in the balloon is greater than a second capacity, the safety valve is closed and liquid injection into the balloon is stopped.

4. The system of claim 2, wherein:
the first pressure sensor is further configured to monitor a pressure value of a balloon wall during a pressurization process or a pressure relief process and send the pressure value of the balloon wall to the main controller; and
the main controller is further configured to identify moments when the pressure value of the balloon wall is equal to zero, sort a liquid pressure corresponding to each of the moments from large to small, determine a liquid pressure at a first position of the sorting as a systolic blood pressure, and determine a liquid pressure at an end position of the sorting as a diastolic blood pressure.

5. The system of claim 2, wherein the main controller is further configured to: determine a current balloon radius according to the capacity of liquid in the balloon and a balloon parameter during the pressurization process or the pressure relief process; and determine a sum of a balloon radius and a balloon thickness as a radius of the blood vessel.

6. The system of claim 2, further comprising a display electrically connected to the main controller and configured to display dilation parameters during the pressurization process and the pressure relief process, wherein the dilation parameters include the first liquid pressure and the liquid flow rate.

7. The system of claim 1, wherein the balloon catheter is provided with a safety valve, and in response to the first liquid pressure being greater than or equal to a second pressure value or in response to determining, according to the liquid flow rate, that the capacity of liquid in the balloon is greater than a second capacity, the safety valve is closed and liquid injection into the balloon is stopped.

8. The system of claim 7, wherein:
the first pressure sensor is further configured to monitor a pressure value of a balloon wall during the pressurization process or a pressure relief process and send the pressure value of the balloon wall to the main controller; and
the main controller is further configured to identify moments when the pressure value of the balloon wall is equal to zero, sort a liquid pressure corresponding to each of the moments from large to small, determine a liquid pressure at a first position of the sorting as a systolic blood pressure, and determine a liquid pressure at an end position of the sorting as a diastolic blood pressure.

9. The system of claim 7, wherein the main controller is further configured to: determine a current balloon radius according to the capacity of liquid in the balloon and a balloon parameter during the pressurization process or the pressure relief process; and determine a sum of a balloon radius and a balloon thickness as a radius of the blood vessel.

10. The system of claim 7, further comprising a display electrically connected to the main controller and configured to display dilation parameters during the pressurization process and the pressure relief process, wherein the dilation parameters include the first liquid pressure and the liquid flow rate.

11. The system of claim 1, wherein:
the first pressure sensor is further configured to monitor a pressure value of a balloon wall during a pressurization process or a pressure relief process and send the pressure value of the balloon wall to the main controller; and
the main controller is further configured to identify moments when the pressure value of the balloon wall is equal to zero, sort a liquid pressure corresponding to each of the moments from large to small, determine a liquid pressure at a first position of the sorting as a systolic pressure of a blood vessel, and determine a liquid pressure at an end position of the sorting as a diastolic pressure of the blood vessel.

12. The system of claim 11, wherein the main controller is further configured to: determine a current balloon radius according to the capacity of liquid in the balloon and a balloon parameter during the pressurization process or the pressure relief process; and determine a sum of a balloon radius and a balloon thickness as a radius of the blood vessel.

13. The system of claim 11, further comprising a display electrically connected to the main controller and configured to display dilation parameters during the pressurization process and the pressure relief process, wherein the dilation parameters include the first liquid pressure and the liquid flow rate.

14. The system of claim 1, wherein the main controller is further configured to: determine a current balloon radius according to the capacity of liquid in the balloon and a balloon parameter during the pressurization process or the pressure relief process; and determine a sum of a balloon radius and a balloon thickness as a radius of the blood vessel.

15. The system of claim 1, wherein the main controller is further configured to: determine an expansion coefficient of a blood vessel according to the capacity of liquid in the balloon and the first liquid pressure during the pressurization process or a pressure relief process; and determine blood vessel elasticity according to the expansion coefficient of the blood vessel.

16. The system of claim 1, further comprising a second pressure sensor connected to a liquid storage device and the main controller and configured to detect a second liquid pressure of the liquid storage device.

17. The system of claim 1, further comprising a display electrically connected to the main controller and configured to display dilation parameters during the pressurization process and the pressure relief process, wherein the dilation parameters include the first liquid pressure and the liquid flow rate.

18. The system of claim 1, wherein the signal collecting module comprises a pedal controller, wherein the pedal controller is electrically connected to the main controller and is configured to collect a pedal control signal and send the pedal control signal to the main controller.

19. The system of claim 1, wherein the signal collecting module comprises an information input sub-module, wherein the information input sub-module is connected to the main controller and is configured to determine the control signal according to an external input command and send the control signal to the main controller.

20. A balloon dilation system, comprising a signal collecting module, a main controller, a pressurization module, a pressure relief module, a first pressure sensor, a flow rate sensor, a balloon catheter and a balloon; wherein
the signal collecting module is electrically connected to the main controller, and is configured to collect a control signal and send the control signal to the main controller;
the main controller is electrically connected to the pressurization module and the pressure relief module separately, and is configured to receive the control signal and control a working state of the pressurization module and a working state of the pressure relief module according to the control signal;

the pressurization module is connected to the balloon through the balloon catheter, and is configured to inject liquid into the balloon through the balloon catheter according to a first control signal of the main controller;

the pressure relief module is connected to the balloon through the balloon catheter, and is configured to discharge liquid in the balloon catheter and the balloon according to a second control signal of the main controller;

the first pressure sensor is arranged on the balloon catheter, and electrically connected to the main controller; and is configured to monitor a first liquid pressure of the balloon and send the first liquid pressure to the main controller;

the flow rate sensor is arranged on the balloon catheter, and electrically connected to the main controller; and is configured to monitor a liquid flow rate of the balloon catheter and send the liquid flow rate to the main controller;

the main controller is configured to determine an expansion coefficient of a blood vessel according to the capacity of liquid in the balloon and the first liquid pressure during a pressurization process or a pressure relief process; and determine blood vessel elasticity according to the expansion coefficient of the blood vessel; and the main controller is further configured to perform at least one of following operations:
 performing at least one of following steps according to the first liquid pressure: adjusting the working state of the pressurization module or adjusting the working state of the pressure relief module; or
 performing at least one of the following steps according to the liquid flow rate: adjusting the working state of the pressurization module or adjusting the working state of the pressure relief module.

\* \* \* \* \*